United States Patent [19]

Furukawa et al.

[11] Patent Number: 5,300,699
[45] Date of Patent: Apr. 5, 1994

[54] PROCESS FOR PREPARING BISPHENOL A OF GOOD HEAT STABILITY

[75] Inventors: Toshihiko Furukawa, Kitakyushu; Katsuhiko Sakura, Kitakyushu; Kiyoshi Hashimoto, Kitakyushu; Nobuaki Egashira, Kitakyushu; Nobuo Moriya; Sachio Asaoka; Nobuyuki Suda; Susumu Yamamoto, all of Yokohama, all of Japan

[73] Assignees: Nippon Steel Chemical Co., Ltd., Tokyo; Chiyoda Corp., Yokohama, both of Japan

[21] Appl. No.: 45,206

[22] Filed: Apr. 13, 1993

[30] Foreign Application Priority Data

Apr. 20, 1992 [JP] Japan .................. 4-126773
Sep. 30, 1992 [JP] Japan .................. 4-283477

[51] Int. Cl.$^5$ .................. C07C 37/70; C07C 39/16
[52] U.S. Cl. .................. 568/724
[58] Field of Search .................. 568/724

[56] References Cited

U.S. PATENT DOCUMENTS 3,936,507 2/1976 Ligorsti et al. .................. 568/724
4,533,764 8/1985 Chang et al. .................. 568/724

FOREIGN PATENT DOCUMENTS 37-10788 8/1937 Japan .
38-18371 9/1963 Japan .................. 568/724
47-43937 7/1972 Japan .
55-79335 6/1980 Japan .................. 568/724

Primary Examiner—Joseph E. Evans
Attorney, Agent, or Firm—Birch, Stewart, Kolasch & Birch

[57] ABSTRACT

This invention relates to a process for preparing bisphenol A of good heat stability by heat-treating bisphenol A containing a very small amount of impurities in a molten state at 185° to 220° C. for 5 to 60 minutes in an oxygen-free atmosphere and the process yields bisphenol A of good heat stability which shows reduced coloration when heated. Bisphenol A prepared by this process has excellent properties relating to color and is particularly suitable as raw material for the manufacture of polycarbonates where the requirement for color is strict.

9 Claims, No Drawings

PROCESS FOR PREPARING BISPHENOL A OF GOOD HEAT STABILITY

FIELD OF THE INVENTION AND RELATED ART STATEMENT

This invention relates to a process for preparing bisphenol A of good heat stability.

Bisphenol A, that is, 2,2-bis(4-hydroxyphenyl)propane, is solid at normal temperature and usually available as colorless or white crystals.

Bisphenol A is frequently used as raw material for polymers such as polycarbonates and hence it is required to decrease the content of impurities in bisphenol A to be as little as possible and be free of coloration. Therefore, in the preparation of polymer-grade bisphenol A, attempts have been made to prevent the coloration of bisphenol A by diminishing the amount of impurities formed as byproducts in the reaction while avoiding exposure to high temperature as much as possible, for example, by applying purification by crystallization with the use of low-boiling solvents. With this method, however, coloring trace impurities remain and they develop color when bisphenol A is heated or when bisphenol A is dissolved in an alkaline solution, a step for the manufacture of polycarbonates. Hence, it is impossible to use bisphenol A containing such impurities as raw material for the manufacture of optical-grade polycarbonates.

A process for decolorizing bisphenol A with thioglycolic acid is described in Japan Tokkyo Koho No. Sho 47-43, 937 (1972). On the other hand, a process in Japan Tokkyo Koho No. Sho 37-10, 788 (1962) describes the addition of phosphates of alkaline earth metals to remove traces of impurities, particularly basic substances, which are considered to accelerate the decomposition of bisphenol A. These processes, however, are not only complicated in their practice but also unable to eliminate the possibility of acids and salts remaining as impurities.

OBJECT AND SUMMARY OF THE INVENTION

The present inventors have conducted extensive studies on what causes bisphenol A to develop color during heating and inferred that the thermal decomposition products of bisphenol A or coloring impurities in traces react with oxygen during heating to develop color. They found, contrary to common knowledge, that heating of the impurities in advance at a temperature in the vicinity of 200° C. in an oxygen-free atmosphere turns them into noncoloring compounds and helps to prevent coloration.

Accordingly, it is an object of this invention to prepare bisphenol A of good heat stability which resists coloration during heating.

Thus, this invention relates to a process for preparing bisphenol A of good heat stability which comprises heat-treating bisphenol A containing traces of impurities in a molten state at 185° to 220° C. in an oxygen-free atmosphere for 5 to 60 minutes.

Bisphenol A is prepared by the reaction of acetone and excess phenol in the presence of an acid catalyst such as hydrochloric acid and acidic cation exchange resins. One of the processes for recovering bisphenol A from the reaction mixture is practiced by removing water, acetone and/or the catalyst from the reaction mixture, cooling the remainder to allow the adduct of bisphenol A and phenol to crystallize out, separating the crystals from the mother liquor, and removing the phenol to recover bisphenol A.

Bisphenol A obtained in this manner may contain a small amount of coloring impurities and show poor heat stability. Bisphenol A to be heat-treated in this invention contains a very small amount, preferably 1,000 ppm or less, more preferably 50~1,000 ppm, of impurities and shows poor heat stability. Preferable as such is bisphenol A which has never received heat treatment at 185° C. or more in the manufacturing step, for example, in the step for removal of phenol. As long as bisphenol A satisfies this condition, it can be a commercial material or an internally manufactured material.

The heat stability as referred to in this invention is typically that of the melt color and can be evaluated by the degree of color developed during heating. In consequence, bisphenol A of better heat stability develops color to a lesser extent upon heating and the degree of coloration is generally expressed by Hazen color number (APHA). It does not matter whether this coloration arises directly from the impurities in bisphenol A or indirectly from their reaction with bisphenol A, but the process of this invention is particularly useful for prevention of coloration supposedly resulting from the oxidation of the impurities.

The heat treatment of bisphenol A is carried out in a molten state at 185° to 220° C. in an atmosphere substantially free of oxygen or, to be specific, in an atmosphere with an oxygen concentration of 0.1% by volume or less. Only a small effect is produced for improving the heat stability at a temperature below 185° C. while thermal decomposition of bisphenol A takes place above 220° C. Color develops during heat treatment in the presence of oxygen. The heat treatment is carried out preferably in an airtight vessel and a period suitable for the treatment is 5 to 60 minutes. The decomposition of bisphenol A occurs if treated longer while the effect is not sufficient if treated shorter.

Those components which are not responsible for the coloration such as phenol may be present at the time of heat treatment. They are removed at the time of heat treatment or before or after that.

Bisphenol A after the heat treatment show improved heat stability and it can be used as it is or after granulation.

According to the process of this invention, a relatively simple heat treatment alone yields bisphenol A of good heat stability which shows reduced coloration during heating. This bisphenol A has excellent properties in respect to color and it can be used advantageously as raw material for the manufacture of polycarbonates where the requirement for color is strict.

DETAILED DESCRIPTION OF THE PREFERRED EMBODIMENTS

This invention will be described below with reference to the accompanying examples. The heat stability of melt color designates the color (APHA; Hazen color number) which develops when 55 g. of the sample is heated at 170° C. and left for a specified period of time.

EXAMPLE 1

Into a container made of glass tube was introduced 55 g. of commercial bisphenol A with a purity of 99.9324% (impurities by wt. ppm; phenol 8, bisphenol A isomers 153, cyclic isopropenylphenol dimer 49, trisphenols 49, and coumarones 10), the container was evacuated and filled with nitrogen, this procedure of evacuating and filling with nitrogen was repeated five times in all, the container was placed in an aluminum block bath which had been heated at 190° C. to melt the bisphenol A while nitrogen was blown into the container and the concentration of oxygen was maintained at 0.1% by volume or less, and the melt was kept under this condition for 30 more minutes to receive the heat treatment.

The container was taken out of the bath and cooled to room temperature while nitrogen was blown in and bisphenol A of improved heat stability was taken out. The bisphenol A was tested for the heat stability of its melt color and the results are shown in Table 1.

EXAMPLE 2

The same procedure as in Example 1 was applied except carrying out the heat treatment at 190° C. for 60 minutes. The results are shown in Table 1.

EXAMPLE 3

Into a container made of glass tube were introduced 55 g. of commercial bisphenol A, the same as used in Example 1, and 25 g. of commercial phenol, the container was placed in an aluminum block bath while nitrogen was blown in, the contents were melted by heating at 125° C., the container was evacuated to 3 Torr while some nitrogen was blown into the container, and the phenol was removed by evaporation under heat. When the temperature reached 190° C., the contents were held at this temperature for 30 minutes to receive the heat treatment. Thereafter, the contents were cooled as in Example 1 and bisphenol A of improved heat stability was taken out. The results are shown in Table 1.

COMPARATIVE EXAMPLE 1

The same procedure as in Example 1 was applied except carrying out the heat treatment at 190° C. for 90 minutes. The results are shown in Table 1.

COMPARATIVE EXAMPLE 2

The same procedure as in Example 1 was applied except carrying out the heat treatment at 230° C. for 30 minutes. The results are shown in Table 1.

COMPARATIVE EXAMPLE 3

The same procedure as in Example 1 was applied except carrying out the heat treatment at 170° C. for 30 minutes. The results are shown in Table 1.

COMPARATIVE EXAMPLE 4

The commercial bisphenol A used in Example 1 was tested for the heat stability of its melt color without heat treatment. The results are shown in Table 1.

TABLE 1

|  | 0 hour | 2 hours | 4 hours | 6 hours |
|---|---|---|---|---|
| Example 1 | 10 | 15~20 | 20~25 | 25 |
| Example 2 | 10~15 | 20 | 25 | 25 |
| Example 3 | 10 | 15 | 20~25 | 25 |
| Comparative example 1 | 20 | 30~35 | 40 | 45 |
| Comparative example 2 | 40 | 70 | 100 | 200 |
| Comparative example 3 | 5 | 70 | 100 | 200 |
| Comparative example 4 | 5 | 20 | 30 | 40 |

What is claimed is:

1. A process for preparing bisphenol A of good heat stability which comprises heat-treating bisphenol A containing a very small amount of impurities in a molten state at 185° to 220° C. for 5 to 60 minutes in an oxygen-free atmosphere.

2. A process for preparing bisphenol A of good heat stability as described in claim 1 wherein the bisphenol A contains 1,000 ppm or less of impurities.

3. A process for preparing bisphenol A of good heat stability as described in claim 1 or 2 wherein said heat treatment is carried out in an atmosphere containing 0.1% by volume or less of oxygen.

4. A process according to claim 1, wherein said oxygen-free atmosphere is a nitrogen atmosphere.

5. A process according to claim 1, wherein said heat treatment is conducted at 190° C. for 30 minutes.

6. A process according to claim 1, wherein said heat treatment is conducted at 190° C. for 60 minutes.

7. A process according to claim 1, wherein impurities not responsible for coloration are removed by evaporation during the heat-treating step.

8. A process according to claim 1, wherein said heat-treating step is conducted in an airtight vessel.

9. A process according to claim 8, wherein said oxygen-free atmosphere is obtained by repeatedly evacuating said airtight vessel and filling it with nitrogen.

* * * * *